(12) United States Patent
Barbeau

(10) Patent No.: US 7,728,133 B2
(45) Date of Patent: Jun. 1, 2010

(54) STABLE PHARMACEUTICAL COMPOSITIONS

(76) Inventor: Donald L. Barbeau, 6 Williamsburg Cir., Evanston, IL (US) 60203

( * ) Notice: Subject to any disclaimer, the term of this patent is extended or adjusted under 35 U.S.C. 154(b) by 0 days.

(21) Appl. No.: 10/987,959

(22) Filed: Nov. 12, 2004

(65) Prior Publication Data

US 2005/0130975 A1 Jun. 16, 2005

Related U.S. Application Data

(60) Division of application No. 10/306,196, filed on Nov. 27, 2002, now Pat. No. 6,821,974, which is a continuation-in-part of application No. 10/087,951, filed on Mar. 5, 2002, now Pat. No. 6,825,196.

(51) Int. Cl.
C07D 237/30 (2006.01)
(52) U.S. Cl. ..................................... 544/237
(58) Field of Classification Search ................ 544/235, 544/237
See application file for complete search history.

(56) References Cited

U.S. PATENT DOCUMENTS

| 2,484,029 | A |   | 10/1949 | Hartman et al. |         |
|-----------|---|---|---------|----------------|---------|
| 3,840,639 | A |   | 10/1974 | Ueno et al.    |         |
| 3,978,057 | A |   | 8/1976  | Anderson et al.|         |
| 4,002,753 | A |   | 1/1977  | Carpi et al.   |         |
| 4,061,636 | A | * | 12/1977 | Wise et al.    | 544/237 |
| 4,478,837 | A |   | 10/1984 | Schenker       |         |
| 4,757,142 | A |   | 7/1988  | Pinza et al.   |         |
| 6,821,974 | B2| * | 11/2004 | Barbeau        | 514/248 |
| 6,825,196 | B2| * | 11/2004 | Barbeau        | 514/248 |

OTHER PUBLICATIONS

Reece et al, Selective HPLC assays for hydralazine, J. Chromat., 181, pp. 427-440, 1980.*
Lacagnin et al, Separation and quantitation of hydralazine metabolites by HPLC, Biochem. Pharmacology, 377, pp. 319-327, 1986.*
Druey et al, Hypotensive hydrazinophthalazines and related compounds, J. Medicinal and Pharmaceutical Chemistry, 1959, vol. 1 No. 1, pp. 1-21.*
Joshi et al. (Studies on 4-thiozolidinones—synthesis and pharmacological activity for 1,4-bis[2'-methyl /ethyl/phenyl-subsituted styryl-5'H/methyl/carboxymethyl-4'-thiazolidinon-3'-ylamino]phthalazines, Indian Journal of Chemistry, Section B: Organic Chemistry Including Medicinal Chemistry, 2000, 39B (12), 967-970). ABS.*
Upadhyay et al. (Some new b-lactams and their pharmacological activity, J. of Institute of chemists (India), 1999, 71(5), pp. 173-175). ABS.*
Gupta et al. (Biscyclopentadienyltitanium/zirconium IVderivatives with Schiff bases derived from 1,4-dihydrazinophthalazine, Synthesis and Reactivity in inorganic and metal-organic chemistry, 1995, 25(7), 1177-89). ABS.*
Upadhyay et al. (Potential chemotherapeutic agents, Indian Drugs, 1991, 29(3), 114-6). ABS.*
Mandal et al. (Binuclear copper (II) complexes of some sexadentate phthalazine-hydrazone ligands with strong antiferromagnetic exchange, Inorganic Chimica Acta, 1990, 178 (2), 169-78) ABS.*
Okur (Template reactions of 1,4-bis-alpha-carboxybenzylidenehydrazinophtalazine with cobalt, nickel, and chromium, J. of the Chemical Society, Dalton Transactions: Inorganic Chemistry, 1972-1999, 1988, 9, 2293-5)-ABS.*
Prescott (Thiosemicarbazones and hydrazones of alpha-methylchalone as potential chemotherapeutic agents, International J. of Clinical Pharmacology and Biopharmacy, 1975, 11(4), 332-5)-ABS.*
Maeda et al (Effects of vasodilators on the platelet aggregation and PGI2 generation of vessel wall, Ketsueki to Myakkan, 1983, 14 nol 1, 65-69)—ABS.*

(Continued)

Primary Examiner—Alton N Pryor
(74) Attorney, Agent, or Firm—Schiff Hardin LLP

(57) ABSTRACT

Pharmaceutical compounds having the general formula:

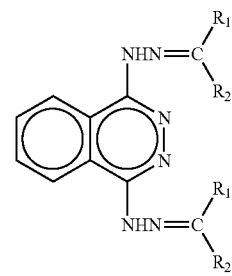

or compounds having the formula:

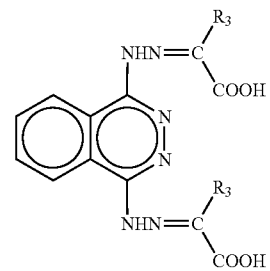

where $R_1$ and $R_2$ are independently H, branched or straight chain alkyl having from 1 to about 7 carbon atoms, substituted or unsubstituted aryl, substituted or unsubstituted cycloalkyl, substituted or unsubstituted aralkyl, substituted or unsubstituted alkylcycloalkyl, lower alkenyl or $R_1$ and $R_2$ together form part of a substituted or unsubstituted cycloalkyl having from about 4 of about 7 carbon atoms; where $R_3$ is a branched or straight chain alkyl having from 1 to about 7 carbon atoms, substituted or unsubstituted aryl, substituted or unsubstituted aralkyl, substituted or unsubstituted cycloalkyl, aralkyl, substituted or unsubstituted alkylcycloalkyl or a group having the formula $(CH_2)_n COOH$ where n is from 1 to about 7.

14 Claims, No Drawings

OTHER PUBLICATIONS

Haegele et al. (Identification of hydrallazine and hydrallazine hydrazone metabolites in human body fluids and quantitative in vitro comparisons of their smooth muscle relaxant activity, British J. of Clinical Pharmacology, 1978, 5 No. 6, 489-94)-ABS.*

Prescott et al, 1,4-Phthalazinediyldihydrazones as potential chemotherapeutic agents, Antimicrobial Agents and Chemotherapy, 1961-70, 1970, vol. date 1969, 262-7. ABS.*

Druery J. and Marxer A., "Hypotensive Hydrazinophthalazines and Related Compounds", Journal of Medicinal and Pharmaceutical Chemistry 1(1): 1-21 (1959) Johnson Reprint Corporation New York.

Shepherd A. et al., "Hydralazine kinetics after single and repeated oral doses", Clinical Pharmacology and Therapeutics 28(6): 804-811 (1980).

Ludden T.M. et al., "Hydralazine kinetics in hypertensive patients after intravenous administration", Clinical Pharmacology and Therapeutics 28(6): 736-742 (1980).

Haegele K.D. et al., "Quantitative Analysis of Hydralazine Pyruvic Acid Hydrazone, The Major Plasma Metabolite of Hydralazine", Journal of Chromatography, 187: 171-179 (1980).

Clementi, W.A. et al., "Endogenous Generation of Hydralazine from Labile Hydralazine Hydrazones[1]", Journal of Pharmacology and Experimental Therapeutics 222(1): 159-165 (1982).

Ogiso T. et al., "Pharmacokinetics of Formation and Excretion of Some Metabolites of Hydralazine and Their Hypotensive Effect in Rats", Journal of Pharmacology and Experimental Therapeutics 233(2): 485-490 (1985).

Iwaki M. et al., "In Vitro Kinetic Studies of the Reaction of Hydralazine and its Acetone Hydrazone with Pyruvic Acid", Journal of Pharmaceutical Sciences 77(3): 280-283 (1988).

McLean A. J. et al., "Interaction of Hydralazine and Hydrazone Derivatives with Contractile Mechanisms in Rabbit Aortic Smooth Muscle[1]", Journal of Pharmacology and Experimental Therapeutics 205(2): 418-425 (1978).

Haegele, K.D. et al., "Identification of Hydrallazine and Hycirallazine Hydrazone Metabolites in Human Body Fluids and Quantitative In Vitro Comparisons of their Smooth Muscle Relaxant Activity", British Journal of Clinical Pharmacology 5: 489-494 (1978).

Barron K. et al., "Comparative Evaluation of the in vitro Effects of Hydralazine and Hydralazine Acetonide on Arterial Smooth Muscle", British Journal of Pharmacology 621: 345-349 (1977).

Israili Z.H. et al., "Metabolism of Hydralazine", Drug, Metabolism Reviews 6(2): 283-305 (1977).

O'Donnell, J.P. et al., "Kinetic Studies of Hydralazine Reaction with Acetaldehyde", Journal of Pharmaceutical Sciences 68(10): 1256-1258(1979).

Zimmer, H., et al., "A Major Metabolite of 1-Hydrazinophthalazine", Arzneim-Forsch 20(10): 1586-1587 (1970).

Talseth, T., Pharmacokinetics and Cardiovascular Effects in Rabbits of a Major Hydralazine Metabolite, the Hydralzine Pyruvic-Acid Hydrazone 211(3): 509-513 (1979).

McLean, A.J. et al., "Study of In Vitro Effects of Hydralazine Metabolites-Comparative Evaluation of Products of Hydroxylation, Hydrolysis and Conjugation", Archives International Pharmacodynamics 235: 19-25 (1978).

LaCagnin, L.B. et al., "Metabolic Activation of Hydralazine by Rat Liver Microsomes", Biochemical Pharmacology 36(16): 2667-2672 (1987).

Lessen, T. et al., "Interactions between Drug Substances and Excipients. 1. Fluorescence and HPLC Studies of Triazolophthalazine Derivatives from Hydralazine Hydrochloride and Starch". Journal of Pharmaceutical Sciences 85(3): 326-329 (1996).

Schneck, D.W. et al., "Plasma levels of free and acid-labile hydralazine: Effects of multiple dosing and of procainamide", Clinical Pharmacology and Therapeutics 24(6): 714-719 (1978).

Talseth T. et al., "Hypotensive Effect of the Hydralazine-Acetone Hydrazone in Conscious Rabbits: Evidence for Its Back-Conversion to Hydralazine In Vivo", Journal of Cardiovascular Pharmacology 4: 370-374 (1982).

McLean, A.J. et al., "Comparative Evaluation of the Hypotensive Activity of Two Major Metabolites of Hydralazine (1-Hydrazinophthalazine)" European Journal of Drug Metabolism and Pharmacokinetics 1: 17-20 (1977).

Juchau, M.R. et al., "Metabolism of Hydrazine Derivatives of Pharmacological Interest", Drug Metabolism Reviews 1(1): 71-100 (1972).

Haegele, K.D. et al., "Determination of Hydralazine and its Metabolites by Gas Chromatography-Mass Spectrometry", Journal of Chromatography 126: 517-534 (1976).

Ludden et al., "High-Pressure Liquid Chromatographic Assay for Hydralazine in Human Plasma", Journal of Pharmaceutical Sciences 68(11) 1423-1425 (1979).

O'Donnell, J.P. et al., "High-Performance Liquid Chromatographic Studies of Reaction of Hydralazine with Biogenic Aldehydes and Ketones", Journal of Pharmaceutical Sciences 68(12) 1524-1526 (1979).

Reece, P.A. et al., "Selective High-Performance Liquid Chromatographic Assays for Hydralazine and Its Metabolites in Plasma of Man", Journal of Chromatography 181, 427-440 (1980).

Lacagnin, L.B. et al., "Separation and Quantitation of Hydralazine Metabolites by High-Performance Liquid Chromatography", Journal of Chromatography, 377, 319-327, (1986).

Iwaki, M. et al., "Pharmacokinetics and Biotransformation of Hydralazine Acetone Hydrazone, a Metabolite of Hydralazine, in the Rat", Journal of Pharmaceutical Sciences 78 (10) 867-873 (1989).

Kanazawa, H. et al., "New Degradation Products in an Aqueous Solution of Hydralazine Hydrochloride with Cirnetidine", Chem. Pharm. Bull. 34 (4), 1840-1842 (1986).

Schuler, W. et al., "Zur Frage Der Spezifitat Der Wirlcung Blutdrucksenkender und . . . ", Arch. Int. pharrnacodyn., CXXVIII, (3-4) 431-468 (1960).

K. Nakashima et al., "Properties of Hydrazones of Hydralazine and Colorimetric Determination of Hydralazine Hydrochloride with p-Dimethylaminocinnamaldehyde Based on Solvent Extraction", Chemical and Pharmaceutical Bulletin, vol. 33, No. 4, 1985 pp. 1515-1521—XP-002365718.

"Stability Problems with Hydralazine p-Anisaldehyde Hydrazone", Journal of Pharmaceutical Sciences, vol. 78, No. 5, May 1989, pp. 432-434—XP008059339.

* cited by examiner

STABLE PHARMACEUTICAL COMPOSITIONS

CROSS-REFERENCE TO RELATED APPLICATIONS

This application is a divisional application of U.S. patent application Ser. No. 10/306,196 filed Nov. 27, 2002 now U.S. Pat. No. 6,821,974 which is a continuation-in-part to patent application Ser. No. 10/087,951 entitles Stable Pharmaceutical Compositions, filed Mar. 5, 2002 now U.S. Pat. No. 6,825,196 in the name of Donald L. Barbeau.

BACKGROUND OF THE INVENTION

The present invention relates to both a novel method of stabilizing hydralazine hydrochloride in pharmaceutical preparations and pharmaceutical compositions containing stabilized hydralazine compounds having the general formula:

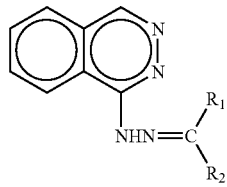

or compounds having the formula:

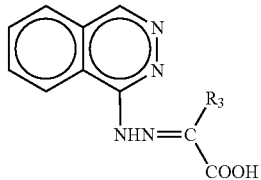

where $R_1$ and $R_2$ are independently H, branched straight chain alkyl having from 1 to about 7 carbon atoms, substituted or unsubstituted aryl, substituted or unsubstituted cycloalkyl, substituted or unsubstituted aralkyl, substituted or unsubstituted alkylcycloalkyl, lower alkenyl or $R_1$ and $R_2$ together form part of a substituted or unsubstituted cycloalkyl having from about 4 to about 7 carbon atoms; where $R_3$ is a branched or straight chain alkyl having from 1 to about 7 carbon atoms, substituted or unsubstituted aryl, substituted or unsubstituted aralkyl, substituted or unsubstituted cycloalkyl, aralkyl, substituted or unsubstituted alkylcycloalkyl or a group having the formula $(CH_2)_n COOH$ where n is from 1 to about 7.

Alternatively, the present invention relates to pharmaceutical compositions containing compounds having the general formula:

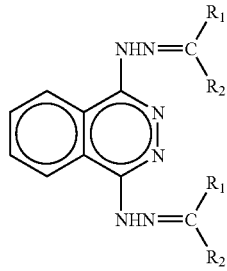

or compounds having the formula:

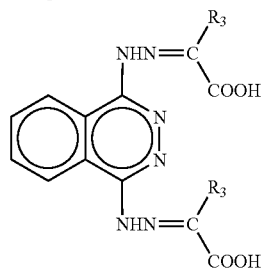

where 1 where $R_1$ and $R_2$ are independently H, branched or straight chain alkyl having from 1 to about 7 carbon atoms, substituted or unsubstituted aryl, substituted or unsubstituted cycloalkyl, substituted or unsubstituted aralkyl, substituted or unsubstituted alkylcycloalkyl, lower alkenyl or $R_1$ and $R_2$ together form part of a substituted or unsubstituted cycloalkyl having from about 4 of about 7 carbon atoms; where $R_3$ is a branched or straight chain alkyl having from 1 to about 7 carbon atoms, substituted or unsubstituted aryl, substituted or unsubstituted aralkyl, substituted or unsubstituted cycloalkyl, aralkyl, substituted or unsubstituted alkylcycloalkyl or a group having the formula $(CH_2)_n COOH$ where n is from 1 to about 7.

Hydralazine hydrochloride is a peripheral vasodilator discovered about 50 years ago that exerts an antihypertensive effect directly on vascular smooth muscle producing relaxation of muscle fibers resulting in a decrease in blood pressure. Hydralazine is extensively metabolized in the body to products that are excreted predominantly in the urine, and undergoes N-acetylation, oxidation, hydroxylation, hydrazone formation and conjugation.

Commercially available in both oral and injectable dosage forms, hydralazine is used to lower blood pressure in hypertensive crisis situations and in patients requiring long-term management of their hypertension after the crisis has abated. Hypertensive crisis is a medical emergency that requires immediate therapy for certain patients in hospital emergency rooms, operating rooms and intensive care units.

Hydralazine is an artery specific direct peripheral vasodilator having an onset of action between 10-30 minutes (10-20 minutes given intravenously), a maximum hypotensive effect in 10-80 minutes and duration of action between 3-4 hours. Hydralazine is one of the few injectable antihypertensive drugs that maintain blood flow to kidneys during hypertensive crisis, and the only one to increase blood flow to an already compromised kidney. Although the drug is approved for administration of 20-40 mg doses, there are several clinical hazards associated with the currently available hydralazine formulation. First, the instability of the 20 mg/ml sterile solutions is a serious problem and has frequently caused removal of the product from the market by the FDA. Submicron particles appear in the hydralazine sterile injection solutions during storage for more than 6-12 months. Secondly, the concentrated 20mg/ml dosage form of hydralazine is difficult to administer accurately to patients at the small doses (3-5 mg) required to avoid "overshoot" hypotension. Consequently, these concentrated solutions are generally diluted prior to use in the hospital. Unfortunately, dilution by hospital personnel in an attempt to reduce the administration problems risks alteration of the hydralazine product, metal contamination and generation of toxic substances. Commercially available hydralazine solutions discolor when inappropriately diluted with metal-containing or carbohydrate-containing diluents generally found in hospitals. The Food and Drug Administration (FDA)s labeling for the currently available hydralazine formulation indicates that hydralazine should not be added to infusion solutions, and that hydralazine hydrochloride injections may discolor upon contact with metal. The FDA further warns in the product labeling that discolored solutions should be discarded.

Hypertensive crisis is a life-threatening situation and includes hypertensive emergencies and hypertensive urgencies characterized by acute elevations in blood pressure, which must be brought under control within hours. Over 60 million people in the United States suffer from essential hypertension. About 1% of these people suffers from hypertensive crisis and requires hospital-based acute care. Of the hypertensive crisis patients, 76% are "urgencies" and 24% "emergencies" with end-organ damage. Hypertensive urgencies are those situations in which it is desirable to reduce blood pressure quickly; however, hypertensive urgencies can be managed without requiring rapid, controlled reduction of blood pressure. Elevated blood pressure alone, in the absence of symptoms or progressive target organ damage rarely requires emergency treatment. Hypertensive urgencies are treated with oral antihypertensives such as nifedipine or clonidine, or with intravenous labetolol.

Hypertensive emergencies are characterized by acute elevations in blood pressure (diastolic >110 to 120 mm Hg) which can potentially be life threatening and thus require rapid, controlled reduction of blood pressure. Prompt pharmacologic therapy is indicated for those patients having Stage 2 ($\geq$160/100 mm Hg) or Stage 3 ($\geq$180/110 mm Hg) hypertension who have clinically manifested cardiovascular disease or target organ damage. The most commonly used antihypertensive agent is nitroprusside. Although hydralazine is already labeled for severe essential hypertension when oral hydralazine cannot be given or when the need to lower blood pressure is urgent as in hypertensive crisis, it is not currently labeled for hypertensive emergencies when a patient presents with emergent end-organ damage. As a patient's blood pressure is acutely elevated, the patient experiences a dramatic decrease in blood flow to vital tissues such as the kidney and brain. The reduction in elevated blood pressure in these patients through antihypertensive therapy is important because it minimizes ischemic damage resulting from reduced blood flow to these tissues. Examples of emergent end-organ damage include hypertensive encephalopathy, cerebral infarction, intracranial hemorrhage, myocardial ischemia, acute pulmonary edema, hypertensive nephropathy, hypertensive retinopathy and eclampsia. The goal of therapy in hypertensive emergencies is to reduce the mean arterial pressure by no more than 25 percent with two hours, then toward 160/110 mm Hg within 2 to 6 hours avoiding excessive drops in pressure that may precipitate or aggravate renal, cerebral or coronary ischemia. Ultimately, the goal of therapy is to reduce the blood pressure to below 140/90 mm Hg.

Hydralazine hydrochloride is very unstable in all of the injectable pharmaceutical formulations currently commercially available. Continuing instability problems with injectable hydralazine hydrochloride, for example, have plagued pharmaceutical manufacturers for many years, forcing these companies to remove their injectable hydralazine products from the marketplace. Although a shelf life of 12 months is currently required for FDA approval for injectable hydralazine hydrochloride, only a few companies have been able to satisfy this requirement with adequate stability data. One such company, SoloPak Pharmaceuticals, Inc. was able to meet the 12-month stability requirements for FDA approval; however, the company was not able to provide a drug product that was consistently stable for more than 6 months.

In its injectable formulation, hydralazine forms small yellow-green particles following storage from 1 to about 2 months when hydralazine is stored at 40° C. and after from 6 to about 9 months storage at 25° C. Although the identification of the yellow-green particles has yet to be confirmed, it is believed that the particles are insoluble polymeric products formed during storage of hydralazine. It is believed that hydralazine hydrochloride undergoes degradation in stored sterile injectable solutions to insoluble polymeric products due to the highly reactive hydrazino group. Hydralazine hydrochloride also undergoes several pharmaceutically undesirable reactions such as chelation with metal ions, oxidation, and pH-dependent decomposition. It is believed that these reactions, which often cause discoloration of hydralazine compositions, are also due to the highly reactive hydrazino group.

Kanazawa et al. [Chemical and Pharmaceutical Bulletin 34(4):1840-1842 (1996)] report that during the storage of a prescription admixture of pulverized hydralazine hydrochloride with cimetidine, a histamine $H_2$-receptor antagonist for duodenal ulcer, the initially uncolored admixture gradually turns to pale yellow. Kanazawa et al. further report that hydralazine hydrochloride undergoes degradation and discoloration with cimetidine in aqueous solution to give 1,1-di(phthalazin-3-yl)amine, 1,1-di(phthalazin-3-yl)hydrazine, 1-amino-1,2, 2-tri-(phthalazin-3-yl)hydrazine, and 1,1,2-tri(phthalazin-3-yl)hydrazine.

Alexander et al. [American Journal of Hospital Pharmacy 50: 683-686(1993)] report that the degradation of hydralazine hydrochloride in a sugar-containing oral syrup was quite fast and was apparently a first order process. The authors report that sugar (e.g., dextrose and fructose) reduces the stability of hydralazine hydrochloride considerably. Their syrup containing maltitol normally increases the stability of drugs sensitive to the presence of sugars; however, the hydralazine formulation remained unstable at room temperature.

Lessen et al. [Journal of Pharmaceutical sciences 85(3): 326-329(1996)] report that the strength of hydralazine hydrochloride in 10 mg tablets containing starch as an excipient decreases significantly with time and produced fluorescence at 414 nm. Lessen at al. report that, in addition to the usual hydralazine degradants such as phthalazone and phthalazine, these tablet compositions produced triazolophthalazine derivatives.

Hydralazine is known to chelate metal ions. Sinha and Motten [Biochemical and Biophysical Research Communications 105(3): 1044-1051(1982)] report that hydralazine oxidizes rapidly in the presence of oxygen and metal compounds such as $Cu^{+2}$, $Fe^{+2}$, and $Fe^{+3}$ through free radical intermediates much like other hydrazine derivatives.

Because of its reactivity toward metals, standard manufacturing requirement for the preparation of bulk hydralazine solution or sterile fill solution is that neither should come into contact with any metal surface including tanks, transfer lines or filling lines. Unfortunately, these precautions can be consistently enforced by the manufacturer only during preparation and storage of the hydralazine solutions. After storage of the hydralazine solutions, the handling of the hydralazine solutions is no longer under their control.

Despite its unique pharmacologic properties as a hypertensive drug, the therapeutic use of hydralazine hydrochloride has been limited by its instability during storage and difficulties in handling by medical personnel. A stable hydralazine pharmaceutical composition that is more easily manufactured and does not degrade or produce particulate matter during extended storage does not currently exist. Moreover, an injectable hydralazine pharmaceutical formulation that is not adversely affected by conventional dilution techniques in the hospital does not currently exist. This, despite the fact that hydralazine was discovered as an antihypertensive agent over 50 years ago. A stable hydralazine composition that could be manufactured more easily and stored for periods of time greater than the current 12 month limit represents a significant advance.

BRIEF SUMMARY OF THE INVENTION

This invention relates to a method of improving the stability of a hydralazine composition during manufacturing or storage comprising coupling an N-protecting group with hydralazine to produce the compound having the formula:

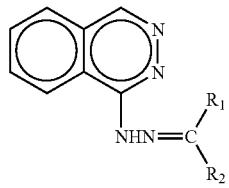

or a compound having the formula:

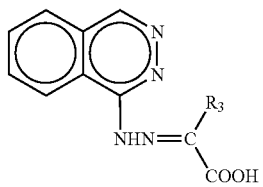

where $R_1$ and $R_2$ are independently H, branched or straight chain alkyl having from 1 to about 7 carbon atoms, substituted or unsubstituted aryl, substituted or unsubstituted cycloalkyl, substituted or unsubstituted aralkyl, substituted or unsubstituted alkylcycloalkyl, lower alkenyl or $R_1$ and $R_2$ together form part of a substituted or unsubstituted cycloalkyl having from about 4 to about 7 carbon atoms; where $R_3$ is a branched or straight chain alkyl having from 1 to about 7 carbon atoms, substituted or unsubstituted aryl, substituted or unsubstituted aralkyl, substituted or unsubstituted cycloalkyl, aralkyl, substituted or unsubstituted alkylcycloalkyl or a group having the formula $(CH_2)_n COOH$ where n is from 1 to about 7; and where said N-protecting group is removed from said compound after manufacturing or storage.

Alternatively, the present invention relates to pharmaceutical compositions containing hydralazine compounds having the general formula:

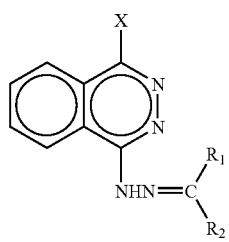

where X is a group having the formula

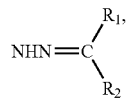

or compounds having the general formula:

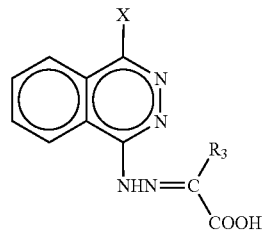

where X is a group having the formula

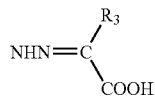

where $R_1$, $R_2$ and $R_3$ having the same meaning as described above.

In particular, the present invention relates to pharmaceutical compositions containing compounds having the formula:

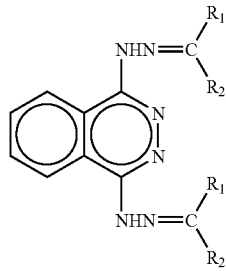

or compounds having the formula:

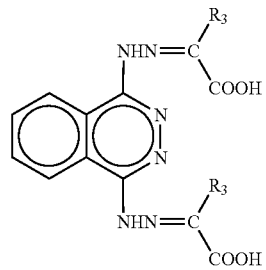

where $R_1$ and $R_2$ are independently H, branched or straight chain alkyl having from 1 to about 7 carbon atoms, substituted or unsubstituted aryl, substituted or unsubstituted cycloalkyl, substituted or unsubstituted aralkyl, substituted or unsubstituted alkylcycloalkyl, lower alkenyl or $R_1$ and $R_2$ together form part of a substituted or unsubstituted cycloalkyl having from about 4 of about 7 carbon atoms; where $R_3$ is a branched or straight chain alkyl having from 1 to about 7 carbon atoms, substituted or unsubstituted aryl, substituted or unsubstituted aralkyl, substituted or unsubstituted cycloalkyl, aralkyl, substituted or unsubstituted alkylcycloalkyl or a group having the formula $(CH_2)_n COOH$ where n is from 1 to about 7.

It is an object of the present invention to stabilize pharmaceutical compositions during manufacturing so that the hydralazine does not react with metal components of the manufacturing system.

It is a further object of the present invention to extend the shelf life of oral and injectable pharmaceutical compositions containing hydralazine significantly beyond 12 months storage and preferably beyond 24 months storage.

It is a further object of the present invention to stabilize injectable pharmaceutical compositions containing hydralazine during storage and reduce the formation of submicron particles.

It is a further object of the present invention to stabilize injectable pharmaceutical compositions containing hydralazine and reduce the discoloration of the hydralazine solution when diluted with conventional pharmaceutical diluents.

It is a further object of the present invention to provide pharmaceutical compositions containing N-protected hydralazine and dihydralazine derivatives in a formulation that is not metabolized by acetylation of the hydrazine group after administration.

DETAILED DESCRIPTION OF THE INVENTION

Compounds in accordance with the one embodiment of the present invention include those containing a non-toxic, biocompatible N-protecting group on the highly reactive hydrazine group of hydralazine represented by the formula:

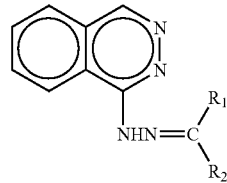

where $R_1$ and $R_2$ are independently H, substituted or unsubstituted branched or straight chain alkyl having from 1 to about 7 carbon atoms, substituted or unsubstituted aryl, substituted or unsubstituted cycloalkyl, substituted or unsubstituted aralkyl, substituted or unsubstituted alkylcycloalkyl, lower alkenyl or $R_1$ and $R_2$ together form part of a substituted or unsubstituted cycloalkyl having from about 4 to about 7 carbon atoms.

In one aspect of the present invention, $R_1$ and $R_2$ are preferably unsubstituted branched or straight chain lower alkyls including but not limited to methyl, ethyl, propyl, isopropyl, butyl, isobutyl, pentyl, isopentyl and hexyl groups. In another aspect of the present invention, $R_1$ and $R_2$ are substituted with hydroxyls. In this embodiment, $R_1$ is H and $R_2$ has the formula $CH_2(CHOH)_m CH_2OH$ where m is 2 or 3.

In one embodiment of the present invention, $R_1$ and $R_2$ are both branched or straight chain lower alkyls. In another embodiment of the present invention, $R_1$ is a substituted or unsubstituted aryl, substituted or unsubstituted cycloalkyl, substituted or unsubstituted aralkyl, substituted or unsubstituted alkylcycloalkyl and $R_2$ is H or lower alkyl. In yet another embodiment of the present invention, $R_1$ and $R_2$ are both substituted or unsubstituted aryl, substituted or unsubstituted cycloalkyl, substituted or unsubstituted aralkyl, substituted or unsubstituted alkylcycloalkyl, lower alkenyl or $R_1$ and $R_2$ together form part of a substituted or unsubstituted cycloalkyl having from about 4 of to about 7 carbon atoms.

The preparation of acetone, 1-phthalazinylhydrazone is described in U.S. Pat. No. 2,484,029 issued on Oct. 11, 1949, which is hereby incorporated by reference; however, no information regarding its stability in aqueous solution is provided.

Compounds in accordance with this embodiment of the present invention are readily prepared by reaction of the carbonyl group of the desired acetone or aldehyde with the highly reactive primary amino group of hydralazine (1-phthalazinylhydrazine). The resulting derivative of hydralazine is generally called a hydrazone. Although aldehydes and ketones are widespread in nature and are generally non-toxic, in preferred embodiments of the present invention these aldehydes and ketones will eventually end up in the patient's plasma after being released from the hydralazine parent compound. Preferably, therefor, the aldehydes and ketones are non-toxic and biocompatible, and do not cause any deleterious effects in animals. Certain aldehydes and ketones have already been recognized as less toxic and of lower risk to human health by the FDA and are referred to as Class 3 compounds. These so-called Class 3 compounds include those not known as a human health hazard at levels normally accepted in pharmaceuticals even though there are no long-term toxicity or carcinogenicity studies for many of the compounds. Available data indicate that they are less toxic in acute or short-term studies and negative in genotoxicity studies. It is considered that small amounts of these compounds in the amount of 50 mg per day or less (corresponding to 5,000 ppm would be acceptable without justification.

These hydrazone forming reactions are generally catalyzed by a small amount of acid, and are buffered to a pH of about 4 to 5. In agreement with general acid catalysis in which the conjugate acid of the carbonyl reactant combines with a free amino group, the rate at which these compounds are formed generally drops at higher and lower pH values. At high pH there will be a vanishingly low concentration of the carbonyl conjugate acid, and at low pH most of the amine reactant will be tied up as its ammonium conjugate acid. In general, these types of derivatization reactions do not require active removal of water, and the products often precipitate from solution as they are formed.

In one embodiment of the present invention, hydralazine derivatives are prepared by coupling an N-protecting group to the terminal nitrogen of the highly reactive hydrazino group on hydralazine to produce a compound having the formula:

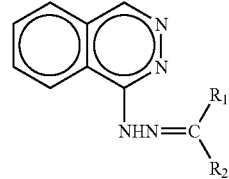

where $R_1$ and $R_2$ are independently H, lower alkyl, or lower alkenyl. Because the hydrazine group readily reacts with the carbonyl group of acetone and aldehydes the N-protected compounds of the present invention can easily be prepared by reacting hydralazine hydrochloride with aldehydes such as formaldehyde and acetaldehyde (I) or ketones such as acetone and other lower alkyl ketones such as butanone (II) as illustrated generally below:

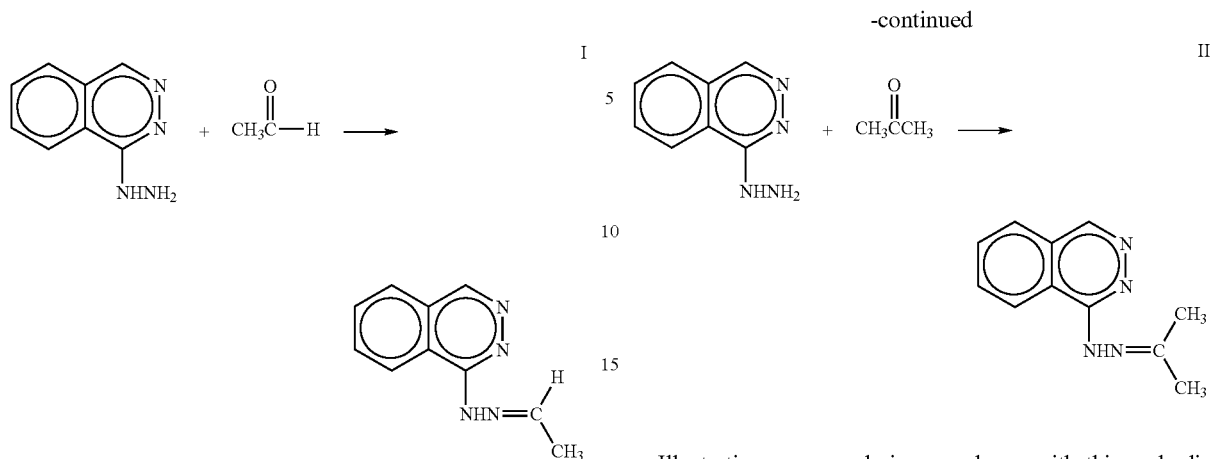

Illustrative compounds in accordance with this embodiment of the present invention are found in Table 1.

TABLE 1

Ketones and Aldehydes

| Compound Number | $R_1$ | $R_2$ | Starting Material |
|---|---|---|---|
| 1 | H | H | formaldehyde |
| 2 | $CH_3$ | H | acetaldehyde |
| 3 | $CH_3$ | $CH_3$ | acetone |
| 4 | $CH_2 CH_3$ | H | propionaldehyde |
| 5 | $CH_2 CH_3$ | $CH_3$ | 2-butanone |
| 6 | $CH_2 CH_3$ | $CH_2 CH_3$ | 3-pentanone |
| 7 | $CH_2 CH_3$ | $CH_2 CH_2 CH_3$ | 3-hexanone |
| 8 | $CH_2 CH_2 CH_3$ | H | 1-butyraldehyde |
| 9 | $CH_2 CH_2 CH_3$ | $CH_3$ | 2-pentanone |
| 10 | $CH_2 CH_2 CH_3$ | $CH_2 CH_2 CH_3$ | 4-heptanone |
| 11 | $CH(CH_3)_2$ | H | 2-methyl propionaldehyde |
| 12 | $CH(CH_3)_2$ | $CH_3$ | 4 methyl butanone |
| 13 | $CH(CH_3)_2$ | $CH_2 CH_3$ | 4 methyl 3-butanone |
| 14 | $CH(CH_3)_2$ | $CH_2 CH_2 CH_3$ | 6-methyl 4-hexanone |
| 15 | $CH(CH_3)_2$ | $CH(CH_3)_2$ | 2,4 dimethyl 3-pentanone |
| 16 | $CH_2 CH(CH_3)_2$ | H | 3-methylbuteraldehyde |
| 17 | $CH_2 CH(CH_3)_2$ | $CH_3$ | 4 methyl pentanone |
| 18 | $CH_2 CH(CH_3)_2$ | $CH_2 CH_3$ | 5 methyl hexanone |
| 19 | $CH_2 CH(CH_3)_2$ | $CH_2 CH_2 CH_3$ | 6 methyl heptanone |
| 20 | $CH_2 CH(CH_3)_2$ | $CH_2 CH(CH_3)_2$ | 1-methyl, 7-methyl 4-heptanone |
| 21 | $CH_2 CH_2 CH_2 CH_3$ | H | valeraldehyde |
| 22 | $CH_2 CH_2 CH_2 CH_3$ | $CH_3$ | 2-hexanone |
| 23 | $CH_2 CH_2 CH_2 CH_3$ | $CH_2 CH_3$ | 3-heptanone |
| 24 | $CH_2 CH_2 CH_2 CH_3$ | $CH_2 CH_2 CH_3$ | 4-octanone |
| 25 | $CH_2 CH_2 CH_2 CH_3$ | $CH_2 CH(CH_3) CH_3$ | 2-methyl 4-octanone |
| 26 | $CH_2 CH_2 CH_2 CH_3$ | $CH_2 CH_2 CH_2 CH_3$ | 5-nananone |
| 27 | $CH_2 CH_2 CH_2 CH_2 CH_3$ | $CH_3$ | 2-heptanone |
| 28 | $CH_2 CH_2 CH_2 CH_2 CH_2 CH_3$ | $CH_3$ | 2-octanone |
| 29 | $CH(CH_2 CH_3)CH_2 CH_3$ | $CH_3$ | 3-ethyl 2-pentanone |
| 30 | $CH(CH_3)CH_2 CH_3$ | $CH_3$ | 3-methyl 2-pentanone |
| 31 | $CH(CH_3)CH(CH_3)CH_2 CH_3$ | H | 2,3-dimethylpentaldehyde |
| 32 | phenyl | $CH_3$ | acetophenone |
| 33 | phenyl | H | benzaldehyde |
| 34 | phenyl | $CH_2 CH_2 CH_2 CH_2 CH_2 CH_3$ | 1-phenyl 1-heptanone |

TABLE 1-continued

Ketones and Aldehydes

| Compound Number | R₁ | R₂ | Starting Material |
|---|---|---|---|
| 35 |  | CH₂CH₂CH₂CH₂CH₂CH₃ | 1-phenyl 1-hexanone |
| 36 |  | H | cyclohexanone |
| 37 | 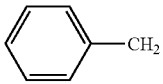 | H | 2-phenylacetaldehyde |
| 38 | 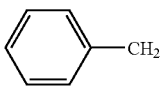 | CH₃ | 3-phenyl 2-propanone |
| 39 | 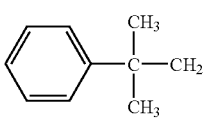 | H | 3-methyl 3-phenylbutyraldehyde |
| 40 | 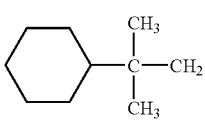 | H | 3-methyl 3-cyclohexylbutyraldehyde |
| 41 | 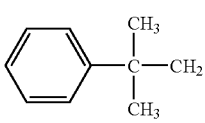 | CH₃ | 4-methyl 4-phenyl 2-pentanone |
| 42 | 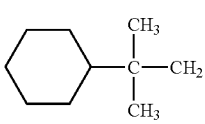 | CH₃ | 4-cyclohexyl 4-methyl 2-pentanone |
| 43 | 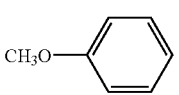 | H | p-methoxybenzaldehyde |
| 44 | CH₃ | CH=C(CH₃)₂ | 1,3-dimethyl-2-butenylidene |
| 45 | H | 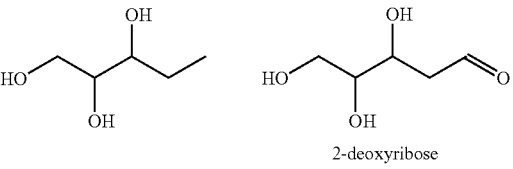 | 2-deoxyribose |
| 46 | H | 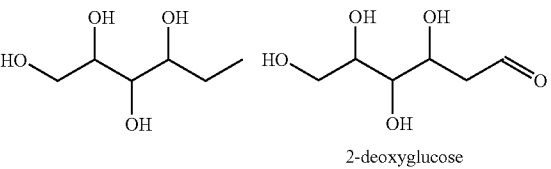 | 2-deoxyglucose |

TABLE 2

| Compound Number | R₁ and R₂ together | Starting Material |
|---|---|---|
| 47 | cyclohexane ring | cyclohexanone |
| 48 | 4-methylcyclohexane ring | 4-methylcyclohexanone |
| 49 | cyclopentane ring | cyclopentanone |
| 50 | 3-methylcyclopentane ring | 3-methylcyclopentanone |
| 51 | cyclobutane ring | cyclobutanone |
| 52 | 3-methylcyclobutane ring | 3-methylcyclobutanone |
| 53 | cycloheptane ring | cycloheptanone |
| 54 | 3-methylcycloheptane ring | 3-methylcycloheptanone |

In another embodiment, hydralazine derivatives are prepared by coupling an N-protecting group to the terminal nitrogen of the highly reactive hydrazine group on hydralazine to produce a compound having the formula:

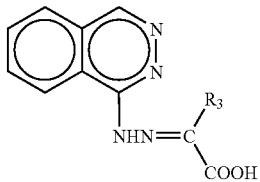

where $R_3$ is a branched or straight chain alkyl having from 1 to about 7 carbon atoms, substituted or unsubstituted aryl, substituted or unsubstituted aralkyl, substituted or unsubstituted cycloalkyl, substituted or unsubstituted aralkyl, substituted or unsubstituted alkylcycloalkyl or a group having the formula $(CH_2)_n COOH$ where n is from 1 to about 7. In accordance with one aspect of this embodiment of the present invention, $R_3$ is a branched or straight chain alkyl having from 1 to about 7 carbon atoms. In accordance with another aspect of this embodiment of the present invention, $R_3$ is a substituted or unsubstituted aryl, substituted or unsubstituted aralkyl, substituted or unsubstituted cycloalkyl, or substituted or unsubstituted alkylcycloalkyl.

Because the hydrazine group readily reacts with the carbonyl group of acids the N-protected compounds of the present invention can easily be prepared by reacting hydralazine hydrochloride with acids such as pyruvic acid (III) α-ketoglutarate (IV) as illustrated generally below:

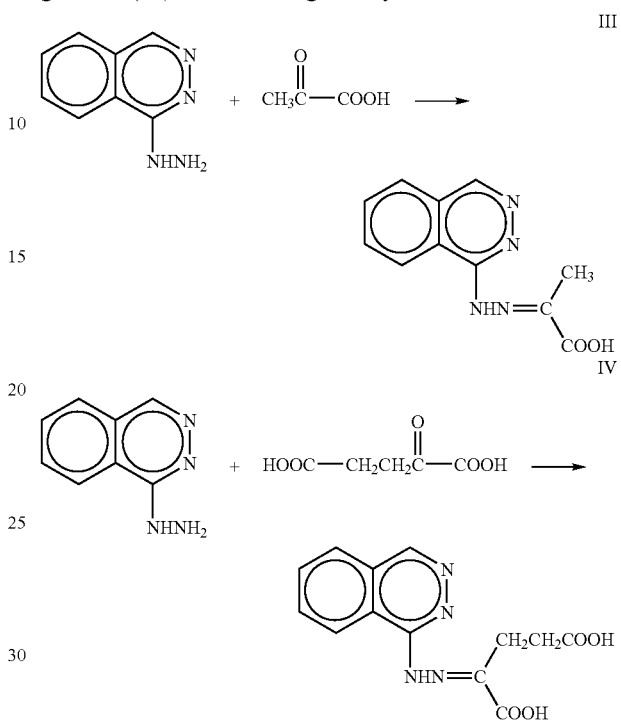

In accordance with a preferred embodiment of the present invention hydralazine derivatives are prepared by coupling an N-protecting group to the terminal nitrogen of the highly reactive hydrazine group on hydralazine to produce a compound having the formula:

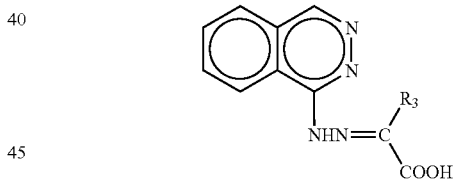

where $R_3$ is a group having the formula $(CH_2)_n COOH$ where n is from 1 to about 4.

Illustrative compounds in accordance with this embodiment of the present invention are found in Table 3.

TABLE 3

Ketoacids

| Compound Number | $R_3$ | Starting Material |
|---|---|---|
| 55 | $CH_3$ | Pyruvic acid |
| 56 | $CH_2 CH_3$ | α-ketobutyric acid |
| 57 | $CH_2 CH_2 CH_3$ | α-ketopentanoic acid |
| 58 | $CH(CH_3)_2$ | α-ketoisovaleric acid |
| 59 | $CH_2 CH(CH_3)_2$ | α-ketoisocaproic acid |

TABLE 3-continued

Ketoacids

| Compound Number | R₃ | Starting Material |
|---|---|---|
| 60 | CH₂CH(CH₃)CH₂CH₃ | 3-ethyl, 3 methyl pyruvic acid |
| 61 | CH₂CH₂CH₂CH₃ | α-ketohexanoic acid |
| 62 | CH₂CH₂CH₂CH₂CH₃ | α-ketoheptanoic acid |
| 63 | CH₂CH₂CH₂CH₂CH₂CH₃ | α-ketooctanoic acid |
| 64 | C₆H₅—CH₂ | α-ketophenyl-pyruvic acid |
| 65 | C₆H₅ | α-ketophenyl-glyoxylic acid |
| 66 | C₆H₅—CH₂CH₂CH₂ | α-keto 4-phenylbutyric acid |
| 67 | CH₃O—C₆H₄ | α-keto p-methoxyphenyl glyoxylic acid |
| 68 | C₆H₅—C(CH₃)₂—CH₂ | 4-methyl, 4-phenyl α-ketopentoic acid |
| 69 | cyclohexyl | α-ketocyclo-hexylglyoxylic acid |
| 70 | CH₂CH₂CH₂CH₂CH₂CH₂CH₂COOH | α-ketodecanedoic acid |
| 71 | CH₂CH₂CH₂CH₂CH₂CH₂COOH | α-ketononanedoic acid |
| 72 | CH₂CH₂CH₂CH₂CH₂COOH | α-ketooctanoic acid |
| 73 | CH₂CH₂CH₂CH₂COOH | α-keto heptanoic acid |
| 74 | CH₂CH₂CH₂COOH | α-keto hexanoic acid |
| 75 | CH₂CH₂COOH | α-ketoglutaric acid |
| 77 | CH₂COOH | α-keto butanedioic acid |
| 78 | COOH | α-keto glyoxalic acid |

Illustrative compounds in accordance with one embodiment of the present invention include the following:

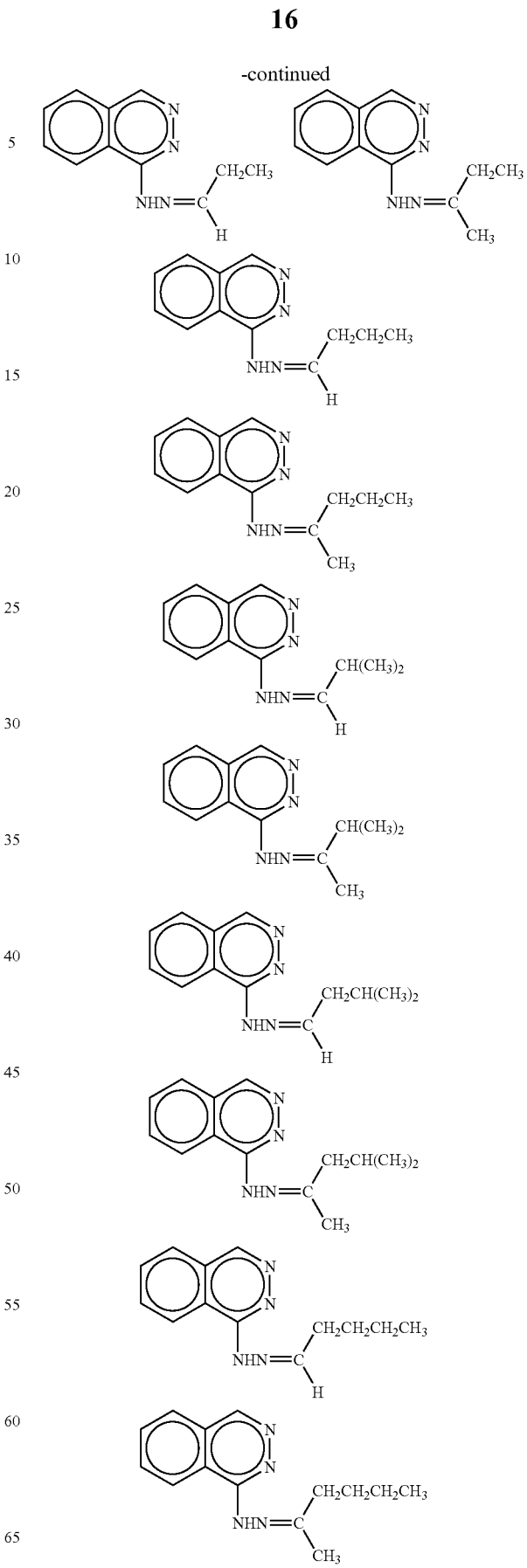

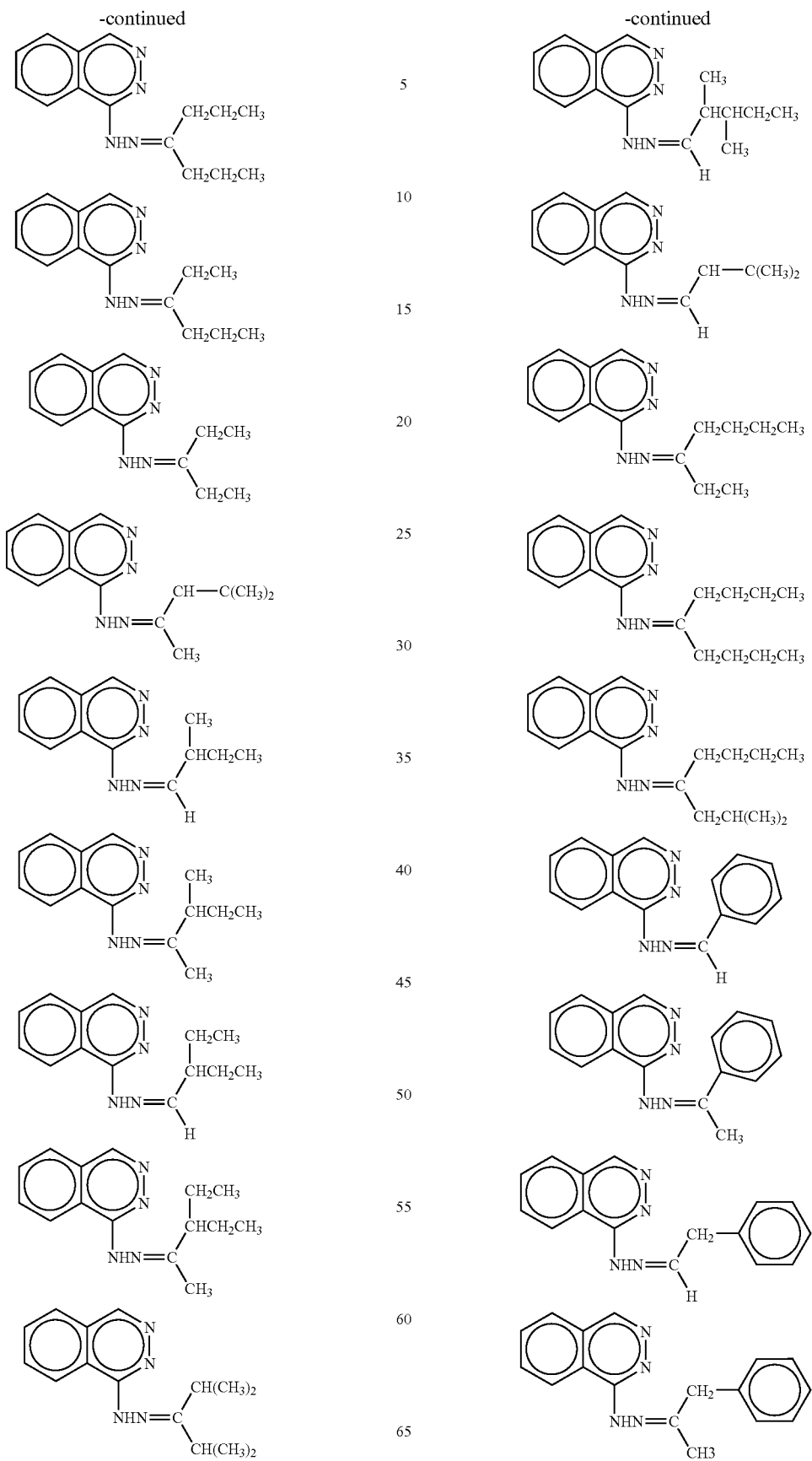

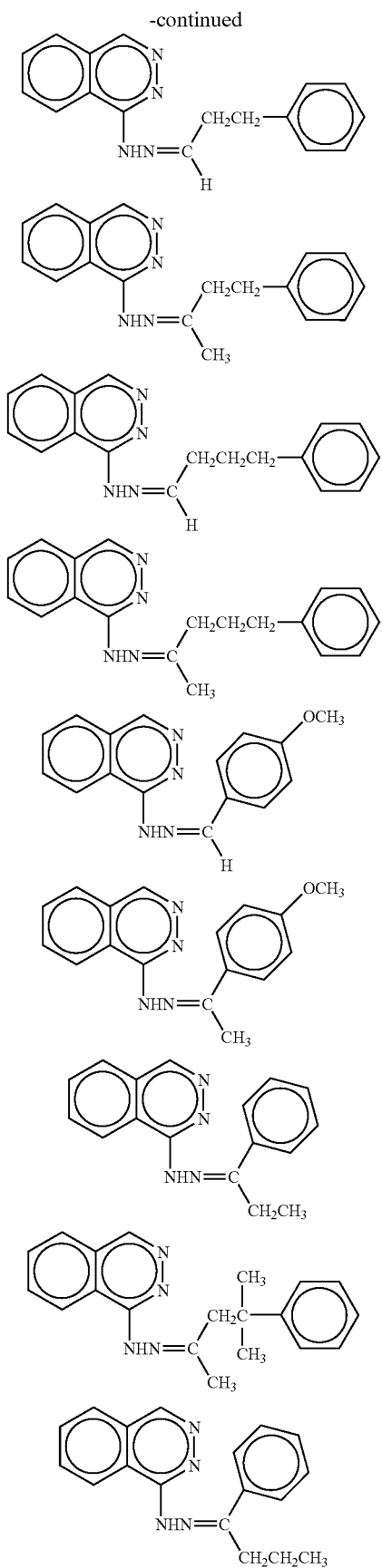
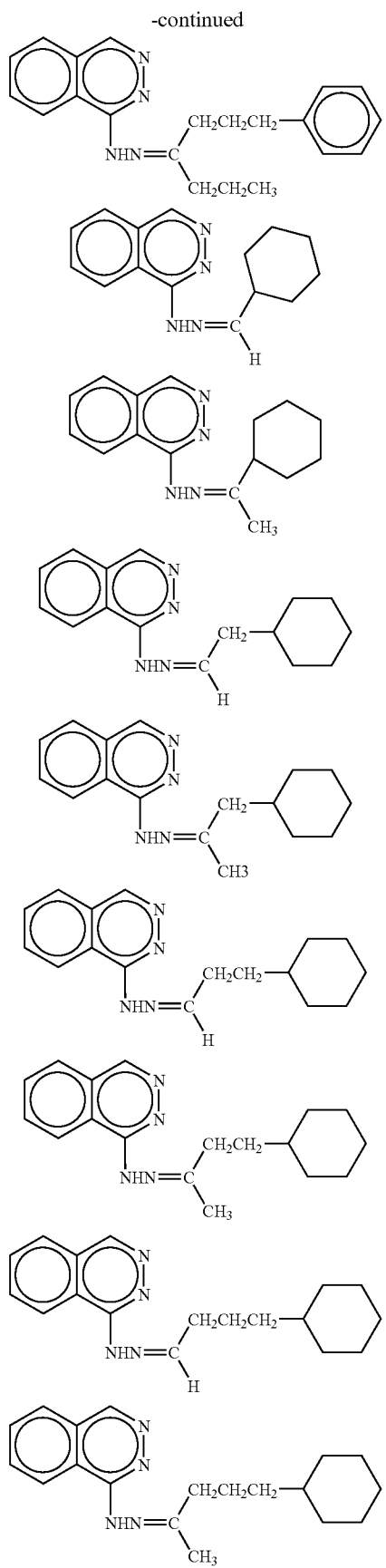

-continued
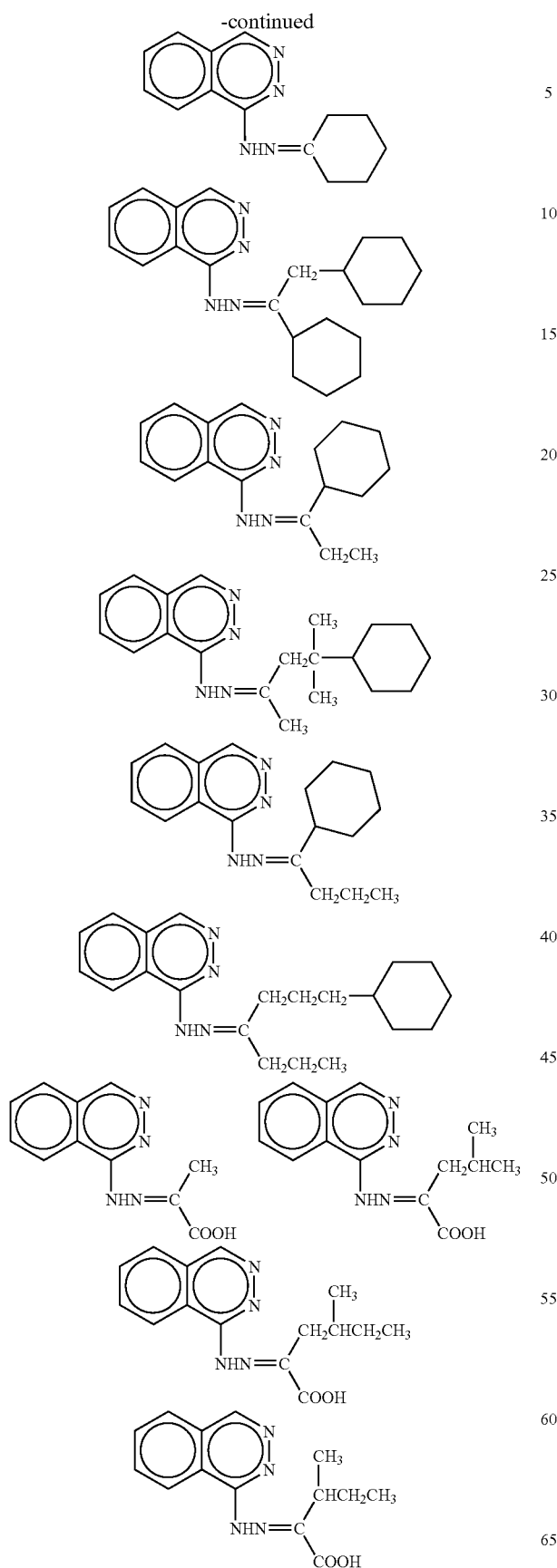
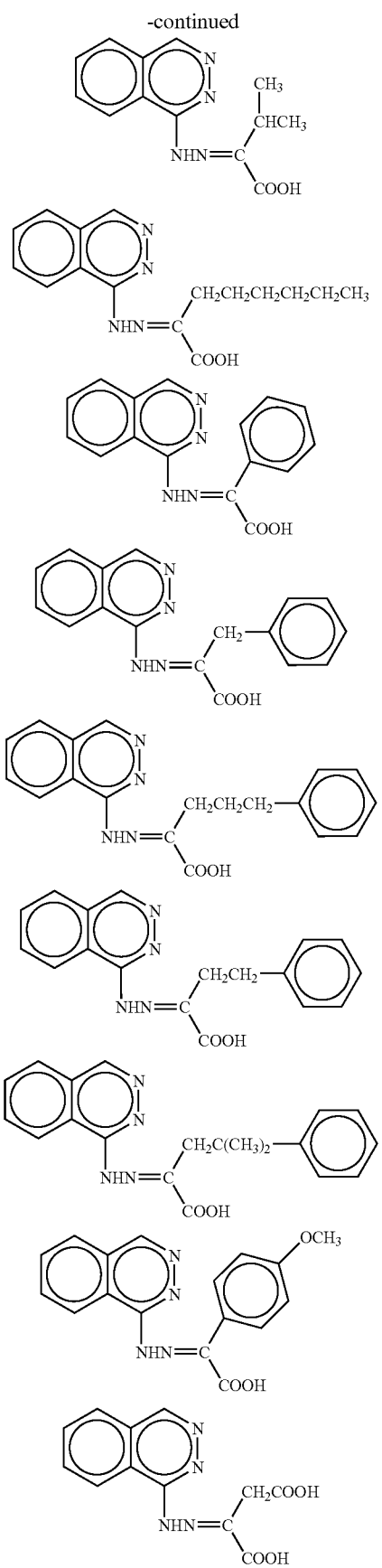

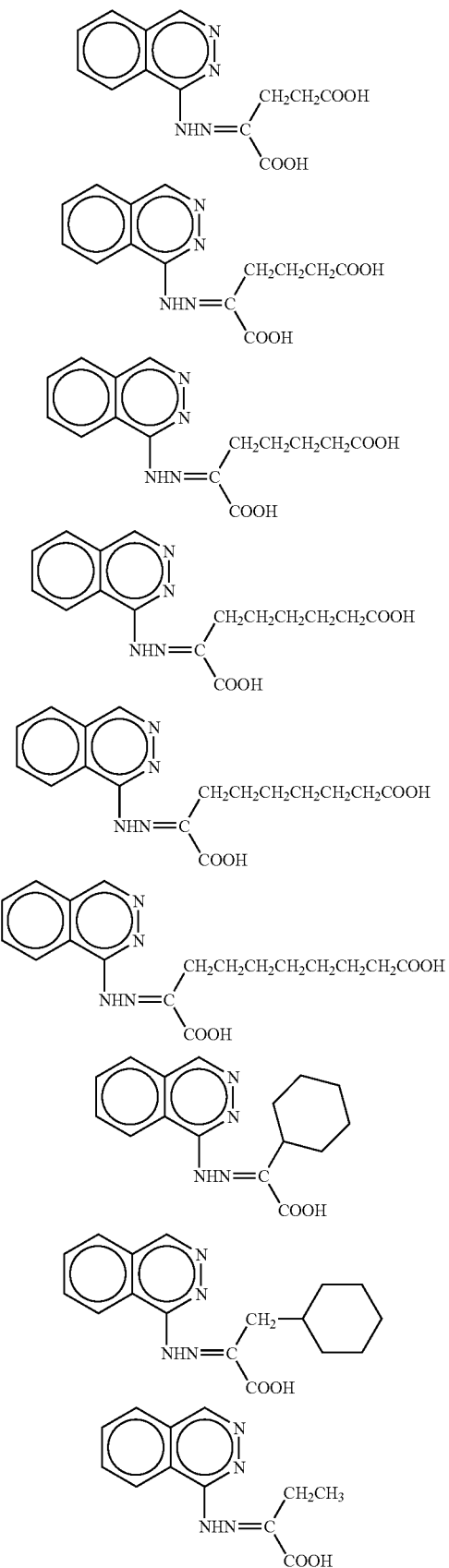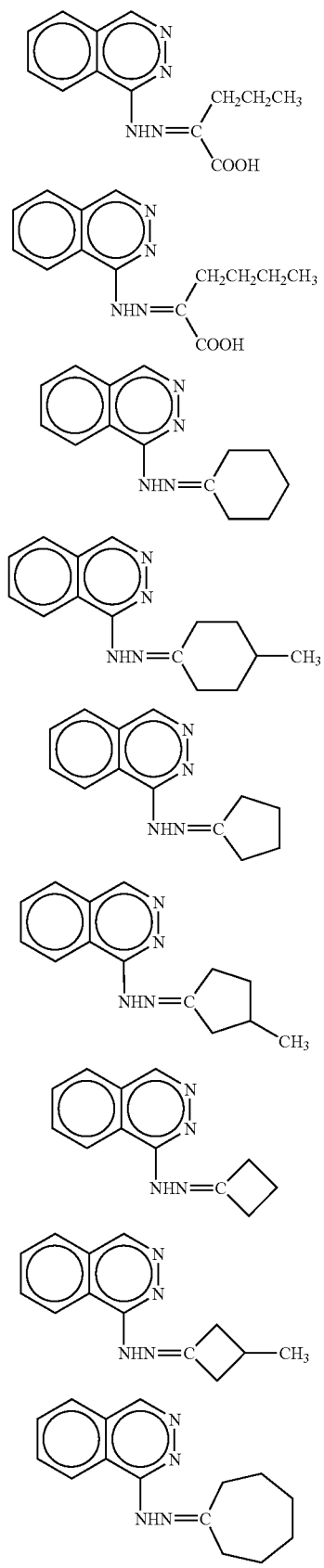

-continued

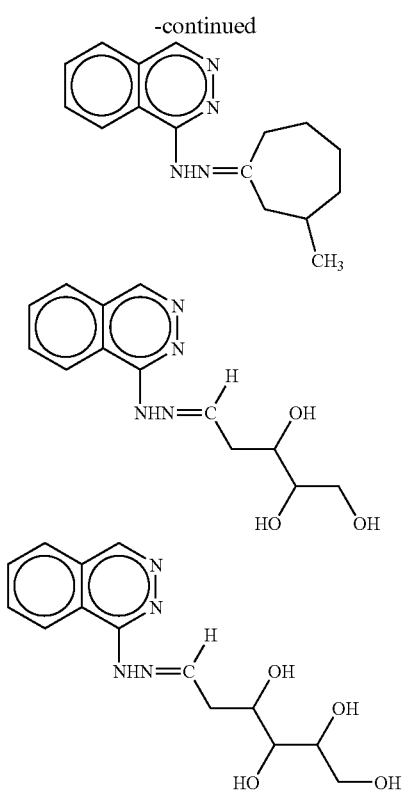

Compounds in accordance with another embodiment of the present invention include the following:

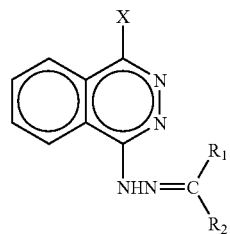

where X is a group having the formula

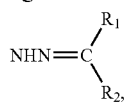

or compounds having the general formula:

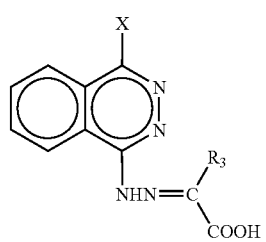

where X is a group having the formula

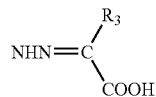

where $R_1$, $R_2$ and $R_3$ having the same meaning as described above.

It will be apparent to those skilled in the art that compounds in accordance with this embodiment of the present invention are similar to those identified in Tables 1, 2 and 3 and can be prepared similarly except that the starting material includes 1,4-hydrazinopthalazine (dihydralazine) instead of hydralazine.

In accordance with the present invention, stability with respect to the hydralazine compositions refers to both the chemical and physical integrity of the composition. Hydralazine hydrochloride, with a pK of about 7.3 is most stable at a pH of about 3.4 to about 4.4, and is unstable at high pH where it degrades into phthalazine, phthalazinone and hydrazine. Because injectable hydralazine pharmaceutical solutions are currently required to contain less than 10 ppm of hydrazine, sterile injectable hydralazine solutions have a pH of between 3.4 and 4.4. Even stored at a pH of about 3.4, sterile injectable hydralazine solutions produce detectable amounts of phthalazine, phthalazinone and hydrazine over time during storage. These sterile injectable hydralazine solutions are filter believed to undergo degradation to insoluble polymeric products through the highly reactive hydrazino group as illustrated below:

Degradation of Hydralazine on Storage

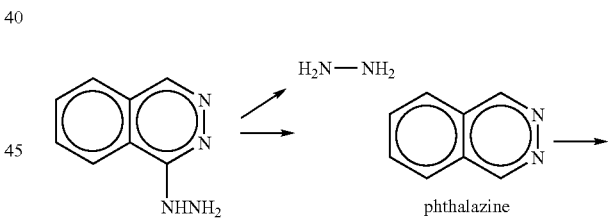

Hydralazine hydrochloride     phthalazine

phthalazinone

Hydralazine hydrochloride

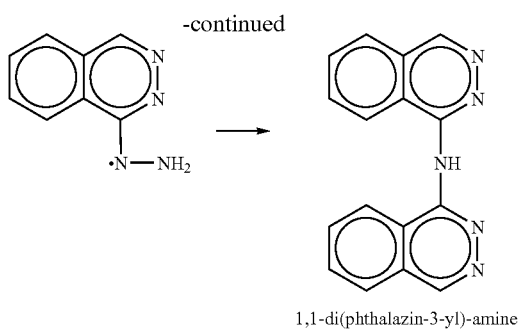

1,1-di(phthalazin-3-yl)-amine

Although confirmation is not yet available, it is believed that formation of the submicron particles in injectable hydralazine solutions results from the insoluble polymers of hydralazine generated through degradation during storage. In accordance with the present invention, the stability of hydralazine compositions during storage is determined by monitoring the degradation products phthalazine, phthalazinone and hydrazine as well as the generation of insoluble polymeric products. Even stored at a pH of 3.4, sterile injectable hydralazine solutions produce detectable amounts of submicron particles over time during storage. In accordance with a most preferred embodiment of the present invention, the stability of the pharmaceutical compositions containing hydralazine is improved such that the shelf life of pharmaceutical compositions containing hydralazine is significantly extended beyond 12 months storage and preferably beyond 24 months storage.

It is an object of the present invention that the stability of the N-protected hydralazine compounds is improved compared to that of unconjugated hydralazine. The stability of the N-protected hydralazine compounds of the present invention varies depending upon the nature of the protecting group; however, many of the compounds in accordance with the present invention are acid-labile. Consequently, these compounds are stored at higher pH. In contrast to the sterile injectable hydralazine solutions which are stored at a pH of about 3.4 to 4.4, the hydralazine containing pharmaceutical compositions in accordance with the present invention are preferable stored at a pH greater than 4.4. In a more preferred embodiment of the present invention, the hydralazine containing pharmaceutical compositions of the present invention are stored at a pH of about 5 to about 8. The pH stability of the compounds of the present invention is easily measured by testing solutions up to 24 months using a HPLC method having a lower limit of sensitivity of 0.0125 uM.

In a preferred embodiment of the present invention, stable hydralazine solutions contain less than about 10 ppm (parts per million) and more preferable less than about 3 ppm hydrazine. In a more preferred embodiment of the present invention, stable hydralazine compositions contain less than about 1% by weight of degradation products including phthalazine and phthalazinone. In a more preferred embodiment of the present invention, stable hydrazine solutions are essentially particle-free. That is, the presence of particulate matter or particles in injectable hydralazine compositions is not detectable by inspecting the hydralazine solutions in both an upright and inverted position. In a most preferred embodiment of the present invention, the formation of submicron particles in liquid pharmaceutical compositions containing hydralazine during storage is significantly reduced and particles are not detectable from about 18 to about 24 months after completion of manufacturing and storage was initiated.

In one embodiment of the present invention, injectable hydralazine formulations do not form small yellow-green particles from 1 to about 2 months after storage when hydralazine is stored at 40° C. and after from 6 to about 9 months storage at 25° C.

In accordance with the present invention, particulate matter consists of mobile randomly sourced extraneous substances, other than gas bubbles, that cannot be quantitated by chemical analysis due to the small amount of material that it represents and to its heterogeneous composition. Particulate matter (particles) in the injectable solutions for parenteral use in accordance with the present invention is determined based on visual inspection and by measured light obscuration procedures. Particles having a diameter of about 50 microns can be measured by visual inspection. The light obscuration procedures are performed for the purpose of enumerating sub-visible extraneous particles having sizes than about 50 microns. In accordance with the present invention, detection of particulate matter by light obscuration is preferably performed with a suitable electronic, liquid-borne particle counting system that uses a light-obscuration sensor with a suitable sample-feeding device. A variety of suitable devices of this type are commercially available.

In accordance with the one embodiment of the present invention, an injectable pharmaceutical composition is considered stable if the average number of particles of about 10 microns in the composition does not exceed 6,000. In accordance with another embodiment of the present invention, an injectable pharmaceutical composition is considered stable if the average number of particles of about 25 microns in the composition does not exceed 600. In accordance with yet another embodiment of the present invention, a pharmaceutical composition is considered stable if no particles are visible. In accordance with a preferred embodiment of the present invention, an injectable hydralazine containing pharmaceutical composition is particle-free if the average number of particles of about 10 microns in the composition does not exceed 6,000, the average number of particles of about 25 microns in the composition does not exceed 600, and no particles are visible.

Acid labile derivatives of hydralazine have been reported by a number of researchers in an effort to identify and characterize the metabolites of hydralazine including Clementi et al. in Journal of Pharmacological and Experimental Therapeutics 222(1): 159-165 (1982) found that certain acid-labile hydralazine derivatives were also plasma labile and are pharmacologically active and are endogenously hydrolyzed to parent hydralazine after intravenous administration. Clementi et al. report that, although differences in the pharmacological properties between the labile derivatives related to the time course of parent hydralazine generation in plasma exist, the hydrolysis of the labile derivatives may be nearly complete. Although differences in the extent and rate of appearance of hydralazine in plasma are reported by Clementi et al., the extent and rate of appearance is therapeutically similar to that of hydralazine after administration of hydralazine. Differences between the stability of hydralazine derivatives in plasma in vitro and the same compounds in vivo suggest that plasma-labile derivatives of hydralazine might be altered in the tissues as well as in the plasma.

The N-protected compounds produced from reaction with ketones, aldehydes or ketoacids in accordance with the present invention are used in the preparation of a pharmaceutical dosage form intended for human use. In the case of manufacturing a sterile injectable dosage form suitable for intravenous administration to a patient, the N-protected compounds are dissolved in an appropriate solution for parenteral administration and filled into bottles, vials, syringes or ampules with a pharmaceutically acceptable diluent under sterile manufacturing conditions. Upon completion of manufacturing this sterile injectable solution, the filled bottles, vials, syringes or ampules are stored under appropriate storage conditions. In the case of an oral dosage form, the N-protected compounds are mixed with pharmaceutically acceptable fillers and excipients in a syrup, capsule or tablet.

In one embodiment of the present invention, the N-protected compounds are formulated in a concentrated sterile solution for dilution at a concentration of from about 10 to about 30 mg/ml (by weight), and preferably at a concentration of about 20 mg/ml. Most preferably, these compounds are formulated in sterile water for injection at a concentration of 20 mg/ml. In accordance with this embodiment of the present invention, the pH of the injection solution during storage is from about 7.4 to about 9.0, and preferably from about 8.0 to 8.5.

In another one embodiment of the present invention, the N-protected compounds are formulated in a more dilute concentration in a sterile solution. In accordance with a preferred embodiment of the present invention, these compounds are formulated at a concentration of from about 0.5 to about 10 mg/ml (by weight), and preferably at a concentration of about 5 mg/ml. Most preferably, these compounds are formulated in sterile water for injection at a concentration of 5 mg/ml.

After storage of the sterile injectable dosage form containing the N-protected compounds of the present invention, the N-protecting group is removed from the parent hydralazine molecule immediately prior to injection into a patient. In one embodiment of the present invention, the pH of the sterile injectable solution containing the acid-labile compound is adjusted so that N-protecting group is released from hydralazine and the N-protecting group remains in the injection solution. This is illustrated by the following reaction scheme:

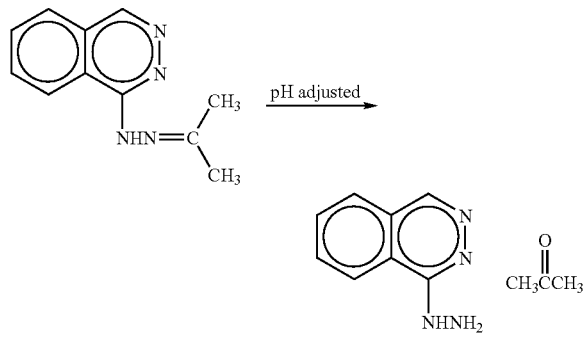

By way of example, a vial containing 2 ml of the N-protected compounds of the present invention formulated in a concentrated sterile solution for dilution at a concentration of about 20 mg/ml at pH 8.0, is diluted prior to use with a sufficient volume of sterile water for injection having a stabilizing effective pH. Preferably, the pH of the diluted solution is from about 3.0 to about 6.0.

Alternatively, the acid-labile compounds of the present invention are formulated into an oral dosage form such as a syrup, capsule or tablet. In this case, the syrup, capsules or tablets containing the N-protecting compounds can be dosed to a patient without prior manipulation of the pH. In this case, as the oral dosage form reaches the highly acidic conditions of the stomach and the N-protecting group is removed from the parent hydralazine molecule prior to absorption. As in another embodiment of the present invention, the N-protecting group is released from hydralazine; however, the N-protecting group will be absorbed and metabolized as it travels through the gastrointestinal system.

In the case of plasma-labile compounds of the present invention, there is no need to adjust the pH of the composition so that N-protecting group is removed from the parent hydralazine compound. In this case, the compounds of the present invention are administered to the patient and the N-protecting group is removed in the plasma after administration such that the extent and rate of appearance of hydralazine in the plasma is therapeutically similar to that of hydralazine after administration. In accordance with the present invention, the plasma-labile compounds are therapeutically similar to hydralazine with regard to vasopressor activity. It is contemplated that some differences in the extent and rate of appearance of hydralazine in the plasma between these plasma-labile compounds and hydralazine will occur. Nevertheless, their extent and rates of appearance in patients are to be considered therapeutically similar if these differences are medically insignificant or these compounds have the same clinical effect when administered to patients when administered under similar clinical conditions.

In yet another aspect of the present invention, the compounds are formulated in an oral pharmaceutical formulation and protected from degradation in the acidic environment of the stomach. This can be accomplished, by way of example, through enteric coating of tablets or capsules containing these compounds or by formulation of these compounds in suitable drug delivery systems that release the pharmaceutical compounds only after the pharmaceutical preparation has passed through the stomach and entered into the small intestine. In this way, the compounds of the present invention are presented to and adsorbed by the intestinal mucosa intact and are only metabolized to the hydralazine compound during or after adsorption. This is particularly advantageous when administering hydralazine in an oral pharmaceutical composition to patients known as slow-acetylators, those having a deficiency of N-acetyl transferase type 2 enzyme (NAT2). In accordance with the present invention, it is contemplated that the protective coatings will perform variably and might release a small portion of the compounds in the stomach; however, a substantial portion of the pharmaceutical formulation will only be released in the intestine. In a preferred embodiment of the present invention, no measurable amounts of the compound are released from the dosage form in the acidic environment of the stomach and substantially all of the pharmaceutical compound bypasses the stomach and is released in the intestine.

In accordance with the present invention and generally known to persons skilled in the art, a pharmaceutical compound is released from its dosage form after dissolution or disintegration of structural components of the dosage form in a manner generally dependent upon its biological environment. For example, a compressed tablet or a capsule is capable of dissolution and/or disintegration in the stomach; in which case, the drug is released into the stomach. On the other hand, an enteric coated tablet or capsule will resist degradation in the stomach and is essentially protected from degradation, (that is) it does not dissolve or disintegrate until it has transited to the more basic environment of the small intestine. Upon reaching the small intestine, the enteric coated tablet or capsule dissolves or disintegrates and its contents are released into the intestine.

In addition to the formation of hydralazine pyruvic acid hydrazone (HPH) the major plasma metabolite of hydralazine, hydralazine undergoes first pass metabolism after oral administration by acetylation of the hydrazine group. This metabolic pathway, which is genetically determined, occurs in the gastrointestinal mucosa and the liver by the transfer of the acetyl group from acetyl coenzyme A to the hydrazinyl group of hydralazine and the formation of the acetylation product (3-methyl-1,2,4-triazolo-(3,4a) phthalazine) known as MTP. MTP undergoes further metabolism by hydroxylation to form 3-hydroxymethyl -1,2,4-triazolo (3,4a) phthalazine (3-OHMTP). Hydralazine is also metabolized by direct hydroxylation to 4-2-acetylhydrazino phhalazin-1-one (N-AcHPZ), which is mostly found in the urine.

N-acetyltransferase (NAT) is one of the major liver enzymes that are involved in biotransformation of drugs and other exogenous substances. It is recognized that biotransformation of xenobiotics containing an aromatic amine or a hydrazine group by N-acetylation is dependent on the N-acetyltransferases enzymes that in humans are expressed by only two different enzymes, known as NAT1 and NAT2. Genetic polymorphism determines a reduction in the activity of the NAT2 enzyme that is observed in slow acetylators. The incidence of slow acetylator phenotype is about 5 to 10% in Asians, 50% in Americans, and 60 to 70% in Northern Europeans. NAT catalyzes the transfer of acetyl group from acetyl coenzyme A to the primary amino group of the acceptor molecule that results in the formation of N-acetyl derivatives. Individual variability in the activity of this enzyme was discovered nearly 40 years ago when marked interindividual variation in the elimination of isoniazid was detected. Further studies revealed that this variation was genetically controlled and that slow acetylators of isoniazid were homozygous for a recessive gene, whereas rapid acetylators were either homozygous or heterozygous for the normal or wild type gene. Likewise, the metabolism of hydralazine after oral administration and formation of the acetylated metabolite is variable among individuals having phenotypic differences in the expression of the NAT2 enzyme, the so-called fast-acetylators and slow-acetylators.

As a consequence of this difference in the metabolism of hydralazine, the fast-acetylators produce different amounts of active hydralazine metabolites than the slow-acetylators, making it difficult to provide the correct dose of hydralazine to a patient in need of hypertensive therapy. Moreover, a greater incidence of drug-induced lupus erythematosus has been associated slow-acetylators than with fast-acetylators after administration of hydralazine. The compounds of the present invention, when administered orally in a dosage form that reaches the intestine intact, eliminate these differences. Because systemic metabolism is dependent on hydroxylation followed by conjugation with glucuronic acid in the liver and is not dependent on the rate of acetylation, the half-life does not differ very much between slow and fast acetylators.

It is an object of the present invention to stabilize pharmaceutical compositions during manufacturing so that the hydralazine does not react with metal components of the manufacturing system. It is a further object of the present invention to stabilize injectable pharmaceutical compositions containing hydralazine and reduce the discoloration of the hydralazine solution when diluted with conventional pharmaceutical diluents containing trace amounts of metals such as of $Cu^{+2}$, $Fe^{+2}$ and $Fe^{+3}$. Accordingly, the N-protected compounds of the present invention have a reduced capacity to complex with or otherwise react with metals in the manufacturing solutions, storage solutions and diluent solutions employed in the hospital. In accordance with the present invention, the pharmaceutical compositions are essentially metal free and contain essentially metal-free hydralazine. The presence of metals complexed with hydralazine, as measured by the presence of color or reactivity with spin-label probes, is a clear indication that the pharmaceutical compositions are not metal free and the compositions do not contain metal-free hydralazine.

EXAMPLE 1

Preparation of 1-hydrazinophthalazine 1-chlorophthalazine (30 parts) is heated for two hours in a mixture of 100 parts by volume of ethyl alcohol and 90 parts by volume of hydrazine hydrate. After filtering, 1-hydrazinophthalazine crystallizes in yellow needles on cooling. The yellow needles are filtered with suction and washed with cold ethyl alcohol, and recrystalized from methyl alcohol (mp 172-178° C.). On warming in alcohol or aqueous hydrochloric acid, the hydrochloride is obtained (mp 273° C.).

EXAMPLE 2

Preparation of 1-hydrazinophthalazine α-ketoglutarate Hydrazone 1-hydrazinophthalazine hydrochloride (395 mg; 2 mmol) is dissolved in 5 ml of water. To this an aqueous solution of α-ketoglutaric acid (1 g; 7 mmol) is added and the reaction mixture is allowed to stand overnight at room temperature. The solid precipitate is filtered off and dried in vacuo to yield 510 mg of I -hydrazinophthalazine a-ketoglutarate hydrazone (88% theoretical yield). [British Journal of Clinical Pharmacology 5: 489-494 (1978)]

EXAMPLE 3

Preparation of 1-hydrazinophthalazine Formaldehyde Hydrazone

Formaldehyde (0.3 g, 6.82 moles) is added with stirring to 500 ml of 0.05 M phosphate buffer at pH 7.4 and 0.5 g (2.54 mmoles) of 1-hydrazinophthalazine at 37° C. The reaction mixture is stirred at 37° C. for 10 min and then filtered. The filtrate is dried in vacuo to yield a solid residue. Recrystalization from chloroform-ether gives 0.440 g (92%) of the 1-hydrazinophthalazine formaldehyde hydrazone as off-white crystals, mp 108-110° C. [Journal of Pharmacological Sciences 68(12):1524-1526 (1979)]

EXAMPLE 4

Preparation of 1-hydrazinophthalazine Acetaldehyde Hydrazone

Acetaldehyde (0.3 g, 6.82 moles) is added with stirring to 500 ml of 0.05 M phosphate buffer at pH 7.4 and 0.5 g (2.54 mmoles) of I -hydrazinophthalazine at 37° C. The reaction mixture is stirred at 37° C. for 10 min and then filtered. The filtrate is dried in vacuo to yield a solid residue. Recrystalization from chloroform-ether gives 0.440 g (92%) of the 1-hydrazinophthalazine acetaldehyde hydrazone as off-white crystals, mp 108-110° C. [Journal of Pharmacological Sciences 68(12):1524-1526 (1979)]

EXAMPLE 5

Preparation of 1-hydrazinophthalazine 2-butanone Hydrazone

A 10 parts 1-hydrazinophthalazine HCL (0.05 Molar) in 50% methanol-water are mixed with 1 part 2-butanone. After evaporation of solvents, 1-hydrazinophthalazine 2-butanone hydrazone is crystallized from ethanol-heptane (78% yield). [The Journal of Pharmacology and Experimental Therapeutics 205 (2): 418-425 (1978)].

EXAMPLE 6

Preparation of 1-hydrazinophthalazine Acetone Hydrazone 1-hydrazinophthalazine HCL (395 mg; 2 mmoles) is dissolved in 2.5 ml of acetone and allowed to react for 1 hour. The solvent is evaporated and the slightly yellow material is dried in vacuo to yield 411 mg of 1-hydrazinophthalazine acetone hydrazone. (99% of theoretical yield). [British Journal of Pharmacology 61: 345-349 (1977)]

EXAMPLE 7

Preparation of 1-hydrazinophthalazine Pyruvate Hydrazone (a)

1-hydrazinophthalazine HCL (5 g; 25 mmoles) is dissolved in 50 ml 0.1 M sodium phosphate buffer pH 7.4, and a solution of sodium pyruvate (11 g; 100 mmoles) in 30 ml of 0.1 M sodium phosphate buffer pH 7.4 is added while stirring vigorously. The solution becomes distinctively yellow almost immediately and the hydrazone is precipitated slowly. After standing overnight at 4° C., the yellow crystalline product is filtered off and washed with cold distilled water. The residue is recrystallized from hot ethanol-water to yield 4.3 g of 1-hydrazinophthalazine pyruvate hydrazone (70% of theoretical yield). [Journal of Chromatography 187:171-179 (1980)]

EXAMPLE 8

Preparation of 1-hydrazinophthalazine Pyruvate Hydrazone (b)

1-hydrazinophthalazine HCL (1 g) is mixed with acetone (0.38 g) in 30 ml water at room temperature and the solution is magnetically stirred for 10 minutes. Precipitated 1-hydrazinophthalazine acetone hydrazone is collected by filtration as yellow crystals and dried over $CaCl_2$ [Journal of Pharmaceutical Sciences 85(3): 326-329 (1996)]

EXAMPLE 9

Preparation of 1-hydrazinophthalazine Anisaldehyde Hydrazone 1-hydrazinophthalazine HCL (395 mg; 2 mmoles) is dissolved in 2.5 ml of anisaldehyde and allowed to react for 1 hour. The solvent is evaporated and the slightly yellow material is dried in vacuo to yield 411 mg of 1-hydrazinophthalazine anisaldehyde hydrazone. [Journal of Chromatography 126: 527-534 (1976)]

EXAMPLE 10

Single Dose Protocol in SHR [spontaneously Hypertensive Rats]

Adult male spontaneously hypertensive rats (SHR) weighing between 250 and 350 g are maintained on standard rat chow and water ad libitum, and are prepared for cardiovascular studies by implantation of chronic aortic and jugular polyethylene catheters. Four days are allowed for recuperation from surgery. Blood pressure is measured and recorded by a Grass model 7D polygraph (Grass Instrument Co., Quincy, Mass.) through individual Statham P23 Gb pressure transducers. An estimate of mean arterial pressure (MAP) is obtained by maximal electronic dampening of the input signal. During blood pressure measurements the animals are placed in Plexiglas cages with minimal restraint. The MAP should range from 150 to 170 mm Hg.

Each rat receives at least three different doses of i. v. bolus injections of hydralazine and the compounds of Examples 2 through 8 dissolved in a solution of sterile water for injection at pH 3.4. Drug administrations are separated by 4 days to permit complete dissipation of drug effect. The volume of each injection is 0.1 ml/100 g by weight for doses of 2.5 through 12.5 umol/kg. At doses of 20 umol/kg or greater, the volume of each injection is increased to 0.2 ml/kg to permit complete solubilization of the N-protected hydralazine compounds. Hydralazine is dissolved in 30% EtOH-0.9% NaCl. After drug administration, vasopressor activity is determined by measuring the mean arterial pressure (MAP) at 2, 4, 6, 8, 10, 15 and 30 min and then every 30 min for 180 min. Dose response results are assessed by comparing the average peak change in MAP after administration at each dose of compound administered.

EXAMPLE 11

Stability of Hydralazine Hydrazones in Storage Solutions

The stability of the N-protected hydralazine compounds of the present invention is tested in solutions having a pH of 3.0, 4.0, 5.0, 6.0 7.0, 8.0, 9.0 and 10.0 using a HPLC method having a lower limit of sensitivity of 0.0125 uM. The amounts of hydrazine, hydralazine and the N-protected hydralazine compounds in an injectable formulation are measured using HPLC immediately after storing the solutions ($T_0$), 1 week, 2 weeks, 1 month, 2 months, 3 months, 6 months, 9 months, 18 months and 24 months after storage at 25° and 60° C. In addition, the stored solutions are visually inspected in both the upright and inverted positions for the presence of particulate matter immediately after storing the solutions ($T_0$), 1 week, 2 weeks, 1 month, 2 months, 3 months, 6 months, 9 months, 18 months and 24 months after storage at 25° and 60° C. The amounts of hydrazine, hydralazine and the N-protected hydralazine compounds in an injectable formulation are also measured using HPLC immediately after storing the solutions ($T_0$), 1 week, 2 weeks, 1 month, 2 months, 4 months, and 6 months after storage at 400 C. In addition, the stored solutions are visually inspected in both the upright and inverted positions for the presence of particulate matter immediately after storing the solutions ($T_0$), 1 week, 2 weeks, 1 month, 2 months, 4 months, and 6 months after storage at 40° C. The presence of particulate matter or small yellow-green particles over time is a measure of stability.

EXAMPLE 12

Lability of Hydralazine Hydrazones in Administration Solutions

The lability of the N-protected hydralazine compounds of the present invention is tested in solutions having a pH of 3.0, 4.0, 5.0, 6.0 7.0, 8.0, 9.0 and 10.0 using a HPLC method having a lower limit of sensitivity of 0.0125 uM. After adjusting the pH of the storage solution containing the N-protected hydralazine compounds, the hydrazones and hydralazine are measured at 10, 20, 30, 60 and 120 minutes.

The present invention has been described in detail using specific examples to illustrate the preferred embodiments of the invention; however, it will be obvious to those skilled in the art that various modifications thereto can be made without departing from the spirit and scope thereof.

I claim:

1. A compound having the formula:

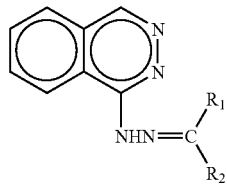

or a compound having the formula:

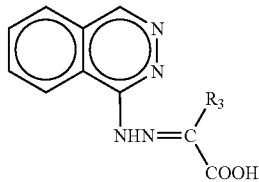

where $R_2$ is H and $R_1$ is substituted cycloalkyl, substituted or unsubstituted aralkyl, or substituted or unsubstituted alkylcycloalkyl; where $R_3$ is substituted or unsubstituted aryl, substituted or unsubstituted aralkyl, substituted or unsubstituted cycloalkyl, substituted or unsubstituted alkylcycloalkyl or a group having the formula $(CH_2)_nCOOH$ where n is from 5 to about 7.

2. A compound having the formula:

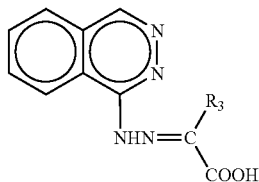

where $R_3$ is substituted or unsubstituted aryl, substituted or unsubstituted aralkyl, substituted or unsubstituted cycloalkyl, substituted or unsubstituted alkylcycloalkyl or a group having the formula $(CH_2)_nCOOH$ where n is from 4 to about 7.

3. The compound of claim 2 wherein $R_3$ is substituted or unsubstituted aryl, substituted or unsubstituted aralkyl, substituted or unsubstituted cycloalkyl, or substituted or unsubstituted alkylcycloalkyl.

4. The compound of claim 2 wherein $R_3$ is a group having the formula $(CH_2)_nCOOH$ where n is from 4 to about 7.

5. A compound having the formula:

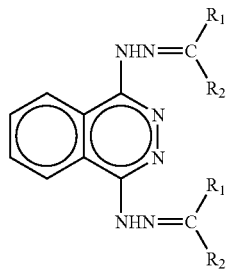

or a compound having the formula:

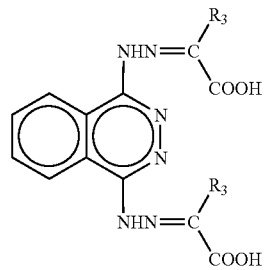

where $R_1$ and $R_2$ are independently H, branched or straight chain alkyl having from 4 to about 7 carbon atoms, unsubstituted aryl, substituted or unsubstituted aralkyl, substituted or unsubstituted alkylcycloalkyl; where $R_3$ is a branched or straight chain alkyl having from 4 to about 7 carbon atoms, substituted or unsubstituted aralkyl, substituted or unsubstituted cycloalkyl, substituted or unsubstituted alkylcycloalkyl or a group having the formula $(CH_2)_nCOOH$ where n is from 3 to about 7; with the proviso that when $R_1$ is H then $R_2$ is substituted or unsubstituted alkylcycloalkyl.

6. The compound of claim 5 wherein $R_1$ and $R_2$ are independently a branched or straight chain alkyl having from 4 to about 7 carbon atoms, substituted or unsubstituted aralkyl, or substituted or unsubstituted alkylcycloalkyl.

7. The compound of claim 5 wherein $R_2$ is H and $R_1$ is a branched or straight chain alkyl having from 4 to about 7 carbon atoms, unsubstituted aryl, substituted or unsubstituted aralkyl, or substituted or unsubstituted alkylcycloalkyl.

8. The compound of claim 7 wherein $R_1$ and $R_2$ are a branched or straight chain alkyl having from 4 to about 7 carbon atoms.

9. The compound of claim 7 wherein $R_1$ is a branched or straight chain alkyl having from about 4 to 7 carbon atoms.

10. The compound of claim 5 wherein said compound has the formula:

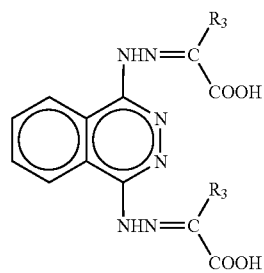

where $R_3$ is a branched or straight chain alkyl having from 4 to about 7 carbon atoms, substituted or unsubstituted aralkyl, substituted or unsubstituted cycloalkyl, substituted or unsubstituted alkylcycloalkyl or a group having the formula $(CH_2)_n$COOH where n is from 3 to about 7.

11. The compound of claim 10 wherein $R_3$ is a branched or straight chain alkyl having from 4 to about 7 carbon atoms, substituted or unsubstituted aralkyl, substituted or unsubstituted cycloalkyl, or substituted or unsubstituted alkylcycloalkyl.

12. The compound of claim 10 wherein $R_3$ is a group having the formula $(CH_2)_nCOOH$ where n is from 3 to about 7.

13. The compound of claim 5 wherein $R_1$ is an unsubstituted aryl, substituted or unsubstituted cycloalkyl, substituted or unsubstituted aralkyl, or substituted or unsubstituted alkylcycloalkyl.
14. A compound having the formula:
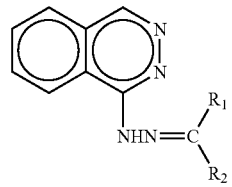
where $R_1$ and $R_2$ are a branched or straight chain alkyl having from about 4 to 7 carbon atoms.
* * * * *